United States Patent
Vija et al.

(10) Patent No.: US 11,903,750 B2
(45) Date of Patent: Feb. 20, 2024

(54) GENERAL PURPOSE, WIDE ENERGY RANGE CALIBRATION SOURCE FOR MEDICAL EMISSION TOMOGRAPHY

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 48 days.

(21) Appl. No.: 17/302,406

(22) Filed: May 3, 2021

(65) Prior Publication Data

US 2022/0346730 A1 Nov. 3, 2022

(51) Int. Cl.
*A61B 6/03* (2006.01)
*A61B 6/00* (2006.01)
*G01T 1/06* (2006.01)

(52) U.S. Cl.
CPC ............... *A61B 6/037* (2013.01); *A61B 6/52* (2013.01); *A61B 6/582* (2013.01); *G01T 1/06* (2013.01)

(58) Field of Classification Search
CPC .......... A61B 6/037; A61B 6/52; A61B 6/582; G01T 1/06
See application file for complete search history.

(56) References Cited

U.S. PATENT DOCUMENTS

| | | | |
|---|---|---|---|
| 6,740,875 B1 * | 5/2004 | Ishikawa | B41M 3/14 250/302 |
| 2006/0224035 A1 * | 10/2006 | Russell, Jr. | A61N 5/1027 600/8 |
| 2010/0202001 A1 * | 8/2010 | Miller | G16H 50/50 358/1.9 |
| 2011/0147574 A1 * | 6/2011 | Blevis | A61B 6/4258 250/252.1 |
| 2013/0092841 A1 * | 4/2013 | Penny | G01T 1/1647 250/362 |
| 2014/0371580 A1 | 12/2014 | Bhattacharya | |
| 2015/0105601 A1 * | 4/2015 | Finger | A61N 5/1017 600/1 |
| 2015/0196268 A1 | 7/2015 | Bhattacharya | |
| 2017/0192104 A1 * | 7/2017 | Bhattacharya | G01T 7/005 |
| 2018/0113226 A1 * | 4/2018 | Naot | G01T 1/1642 |
| 2019/0357872 A1 * | 11/2019 | Ding | G01T 1/2026 |
| 2020/0215355 A1 * | 7/2020 | Olcott | A61N 5/1064 |

FOREIGN PATENT DOCUMENTS

WO WO-2019172997 A1 * 9/2019 ............. A61B 6/037

OTHER PUBLICATIONS

International Patent Application No. PCT/US2020/070520, filed Sep. 10, 2020.
D. E. Bergeron, J. T. Cessna, D. B. Golas, R. K. Young, and B. E. Zimmerman, "Dose calibrator manufacturer-dependent bias in assays of 123I," Applied Radiation and isotopes, vol. 90, pp. 79-83, 201.

* cited by examiner

*Primary Examiner* — Blake C Riddick

(57) ABSTRACT

For calibration in medical emission tomography, the dosimeter and/or detector is calibrated in the field, such as at the clinic or other patient scanning location. To allow for a fewer number of calibration sources used in calibrating and/or assist in calibration for multispectral emission tomography, a calibration source includes multiple isotopes and/or a proxy source or isotope is used instead of the same isotope used in factory calibration.

9 Claims, 3 Drawing Sheets

GENERAL PURPOSE, WIDE ENERGY RANGE CALIBRATION SOURCE FOR MEDICAL EMISSION TOMOGRAPHY

BACKGROUND

The present embodiments relate to calibration for medical emission tomography (e.g., functional) imaging.

Emission tomography imaging uses one or more radioisotopes to determine metabolic function within a patient. For example, the uptake of a radiotracer by tissues in the body is measured. Positron emission tomography (PET) and single photon emission computed tomography (SPECT) are two types of emission tomography imaging. Compton imaging is another type of emission tomography imaging. The emissions from the radiotracer are detected. The activity concentration (i.e., the concentration of the radiotracer from different locations) is reconstructed from the detected emissions.

The reconstruction uses the sensitivity of the detector and/or a calibrated measurement of the injected dose for the emissions. Calibration of emission tomography for absolute quantitative measurement of activity uptake requires the use of calibrated sources for sensitivity calibration of the imaging instrument in specified imaging configuration and cross-calibration to the dosimeter, which measures the dose to be injected into the patient. For many isotopes of clinical interest in diagnostic and/or therapeutic domains, there is currently no cost effective reference source (e.g. no source from NIST or another metrology standards group for commercial use) for calibration.

The current Dosimetry calibration relies on higher energy isotopes such Cs137 for which NIST developed a standard source and is used where the current dosimeter instrument is linear. SPECT imaging occurs in the non-linear region where the correlation between the imaging isotope emission and the calibration isotopes emission is not linear. NIST traceable calibration sources for the non-linear regime have been developed using Co57, Sn157, Tn113 to calibrate the detector for the low, medium and high energy isotopes for SPECT imaging. The sources are used for calibration and/or cross-calibration of dosimeters and emission tomography detectors. Using three sources in the clinic for field calibration is costly. Where isotopes in other energy ranges are to be used, additional calibration sources would be needed at the clinic. Maintaining a large and unwieldy library of sources at the clinic poses a significant cost and periodic upgrade cost due to different half-lives of the many isotopes. Multispectral imaging uses multispectral sources measured with multispectral dose calibrators, resulting in costs for maintaining additional sources at each clinic.

SUMMARY

By way of introduction, the preferred embodiments described below include methods, systems, and calibration sources for calibration in medical emission tomography. In medical emission tomography, the dosimeter and/or detector is calibrated in the field, such as at the clinic or other patient scanning location. To allow for a fewer number of calibration sources used in calibrating and/or assist in calibration for multispectral emission tomography, a calibration source includes multiple isotopes and/or a proxy source or isotope is used instead of the same isotope used in factory calibration.

In a first aspect, a calibration source is provided for medical emission tomography. An epoxy pellet forms an active element with at least two different radioisotopes. A housing encloses the epoxy pellet.

In one embodiment, the active element is a multispectral source with at least one different energy peak for each of the at least two different radioisotopes. In other embodiments, the epoxy pellet is a mix of cured epoxy and the at least two different radioisotopes.

Various geometries may be used for the medical emission tomography calibration source. For example, the epoxy pellet is less than 0.15 inches in a longest dimension, and the housing encloses the epoxy pellet with the epoxy pellet in a first end of the housing. Further, the first end of the housing may form a sphere around the epoxy pellet. An outer diameter of the sphere is less than 0.25 inches. The housing has a second end opposite the first end where the second end forming a cylinder having an outer diameter greater than 0.3 inches.

In another embodiment, the calibration source is a single photon emission computed tomography or positron emission tomography calibration source. In other embodiments, the housing is shaped and sized for placement in a dosimeter.

For use in the proxy source embodiments, the at least two radioisotopes are a first radioisotope common to a factory calibration source and a second radioisotope different than any factory calibration source to be used with a same emission tomography system. For example, the first radioisotope is Co57, Se75, Sn157, Cs137, or Tn113 (or other standards created traceable sources), and the second radioisotope is Lu177, Rh186, St89, Sa153, Bi213, Pb212, Ga157, Bo10, Y90, P32, Ce131, Pa103, Ra223, Ac225, Th232, Po212, I131, Co60, Mn54, Ru106, Rh102, Ag110, Sb125, Cs134, Ce144, Pm146, Pm147, Eu154, Eu155, Tm171, Os194, Tl204, Ra228, Bk249, Es254, Na22, Na24, K42, Mg28, Fe59, Co58, Zn65, or Ca47 (or other sources that may be now used or used in the future (e.g., combined with radiopharmaceutical) for clinical use. Other combinations of isotopes may be provided. The isotopes have a reasonably long half-life, such as greater than 0.5 years but shorter than 10 years. The energies cover the design requirements including expected OPEX for a customer and the instrument to be used.

In a second aspect, a calibration source is provided for medical emission tomography. A first pellet forms a first active element of a first radioisotope. A second pellet forms a second active element of a second radioisotope different than the first radioisotope. A housing encloses the first and second pellets.

In one embodiment, the first pellet is stacked directly adjacent the second pellet within the housing. In other embodiments, the first pellet has a same size and shape as the second pellet.

In a third aspect, a method is provided for calibration of medical emission tomography. An emission tomography detector is provided. The detector was factory calibrated with a first calibrated source of a first radioisotope. The emission tomography detector is field calibrated with a second calibrated source of a second radioisotope. The second radioisotope is different than the first radioisotope. The second calibrated source is a proxy for the first calibrated source.

In one embodiment, the factory calibration was with a National Institute of Standards and Technology traceable calibration source of Co57, Sn157, or Tn113 as the first radioisotope. The field calibration calibrates with the second source of an isotope other than Co57, Sn157, and Tn113.

In another embodiment, the factory calibration was with multiple radioisotopes including the first radioisotope and not including the second radioisotope. The factory calibration was with the multiple radioisotopes calibrating for a respective multiple energy ranges. The field calibrating is calibrating with the second source for one of the multiple energy ranges. For example, the field calibration calibrates for the multiple energy ranges with the second source being a plurality of radioisotopes not including the first radioisotope, including the second radioisotope, and including one of the multiple radioisotopes used in the factory calibrating. In one approach, the field calibration calibrates with the second source having an active element formed as a mixture of the second radioisotope with the one of the multiple radioisotopes used in the factory calibrating. In another approach, the field calibration calibrates with the second source having a first active element of the one of the multiple radioisotopes and a second active element of the second radioisotope. The first and second active elements are encapsulated in a same housing.

In yet another embodiment, a dose calibrator is calibrated with the second source.

The calibration is for emission tomography. In one embodiment using a multispectral source or proxy, the field calibration calibrates the emission tomography detector for multispectral tomography.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A general-purpose multi-energy calibration source allows for less stocking of calibrated sources at clinics. Emission tomography imaging systems are calibrated to reference standards and/or cross-calibrated to dosimeters and dose calibrators for a wide range of emission energies, including multiplexed and Compton imaging systems, using one or a few calibrated sources. A multispectral source and/or proxy source may provide a more cost-sensitive approach to quantitative measurement for isotopes used in diagnostic and/or therapeutic domain for which reference sources are nonexistent.

A singular source with multiple energy lines may cover any energy range and can be used for calibration of emission tomography systems covering the respective field-of-view (FOV) coverage with different implementations. In one embodiment, respective sources (e.g., multiple active elements for different isotopes) are added into one source encapsulation. This one source may be used for calibration in quantitative SPECT (xSPECT) (e.g., an xSPECT quant source). In another embodiment, the epoxy or other substrate forming the active element includes a mixture of various isotopes. For example, isotopes to cover multiple energy ranges of interest are mixed together in the epoxy compound, which is cured to form one active element to be used in the calibration source. In yet another embodiment, a proxy source is used. The factory calibration or class standard may use calibrated sources with particular isotopes. The field calibration of the medical emission tomography system may avoid having to stock sources of all or any of the same isotopes by using a proxy. While using different isotopes for field calibration than was used in factory calibration may result in lesser accuracy and/or precision, fewer calibration sources may need to be stocked at clinical sites.

The proxy or other calibrated source may be adapted in geometry for gas chamber dose calibrators (dosimeters) or a solid-state detector-based imaging dose calibrators. The proxy source may include a mix or active elements for both a proxy isotope and one or more of the isotopes used in factory calibration. The sources providing multiple isotopes (i.e., multispectral sources) may allow for efficient calibration in multispectral tomography, such as multiplexed emission tomography or Compton imaging.

Figure 1:
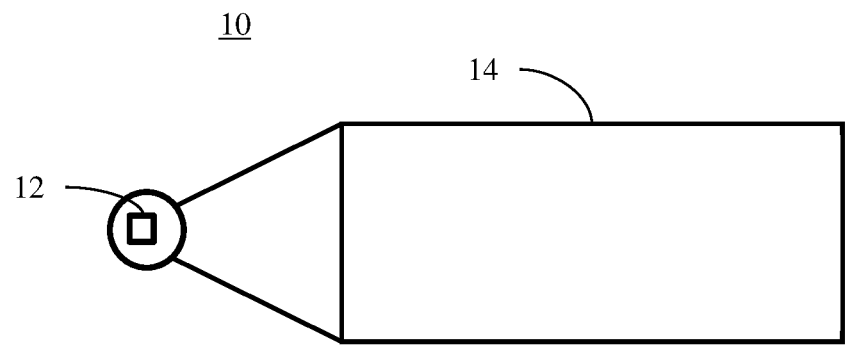
FIG. 1 is a cross-section view of one embodiment of a multispectral calibration source for medical emission tomography imaging.

FIG. 1 is a cross-section view of one embodiment of a calibration source 10 for medical emission tomography. The calibration source 10 is designed as a SPECT, PET, or other emission tomography calibrated source for use in calibrating the detector, the dosimeter, and/or cross-calibration. The calibration source 10 may be provided by a standards organization or manufacturer, such as NIST or another metrology standards group. Alternatively, the calibration source 10 is not from a standards group.

The calibration source 10 includes a known amount of one or more known radioisotopes. The calibration source 10, based on the date of creation, the amount, and the isotopes, emits are known or calibrated amount of radiation or emissions. These known or predictable emissions may be used for field calibration (calibration at a clinical site or location of the emission tomography imager where patients visit).

The calibration source 10 includes a pellet 12 and a housing 14. Additional, different, or fewer components may be provided. For example, a epoxy support for holding the pellet 12 within the housing 14 is provided. As another example, an O-ring or sealant is provided on or in the housing 14.

The pellet 12 forms an active element. The pellet is the source of radio emissions by including one or more radioisotopes. There could be any number of isotopes mixed within a pellet 12. The activity concentration of the epoxy mix can be higher where space is not too much of a concern. The number of gamma lines for calibration may be used to select the included isotopes. For example, if 10 gamma lines all together from 100 keV all the way to 3 MeV are desired, a set of isotopes to cover this range is selected and included in the pellet 12. The separation between the individual gamma lines could be coarser than if the range were 500 keV to 1 MeV. More than one isotope could be used in the same source and calibrated.

In one embodiment, the pellet 12 is cured epoxy. The radioisotope(s) is mixed with the epoxy, and then the epoxy cures to form the active element. Other materials than epoxy may be used, such as a solid block of the isotope material.

Where epoxy is used, more than one radioisotope may be mixed with the epoxy. Powders or liquids of the different radioisotope are mixed at any ratio into the epoxy. Once cured, the resulting pellet 12 is a multispectral source having energy peaks corresponding to the different included radioisotopes. The emission spectrum includes the peak or peaks from each of the included radioisotopes.

None, one, or all of the multiple radioisotopes in the pellet 12 may be the same as radioisotopes used for factory calibration or establishing a class standard. The calibration source 10 may be a source of emissions with the same, all different, or some of the same and some different energies. For example, Co57, Cs137, Sn157, and/or Tn113 are used to calibrate a detector or class of detectors for one or more energy ranges in the factory. The calibration source 10 for field calibration includes one or two of these radioisotopes and also includes a different radioisotope. One or more of the included radioisotopes is different than any factory calibration source that has been and/or is planned to be used with a given emission tomography system. In one embodiment, Co57, Se75, Sn157, Cs137, and Tn113 are used to calibration at the factory in three (low, medium, and high) energy ranges. The calibration source 10 in the field or at the clinical site includes one or more of one Lu177, Rh186, St89, Sa153, Bi213, Pb212, Ga157, Bo10, Y90, P32, Ce131, Pa103, Ra223, Ac225, Th232, Po212, 1131, Co60, Mn54, Ru106, Rh102, Ag110, Sb125, Cs134, Ce144, Pm146, Pm147, Eu154, Eu155, Tm171, Os194, Tl204, Ra228, Bk249, Es254, Na22, Na24, K42, Mg28, Fe59, Co58, Zn65, or Ca47, none of which are used for factory calibration. Other radioisotopes may be used for factory and/or field calibration.

The pellet 12 is shown as a cuboid. Other shapes, such as other polyhedron shapes, may be used. The longest dimension (length, width, or thickness) is less than 0.15 inches but larger pellets 12 may be used. The pellet 12 is formed as a single or contiguous object for emitting radiation.

Figure 2:
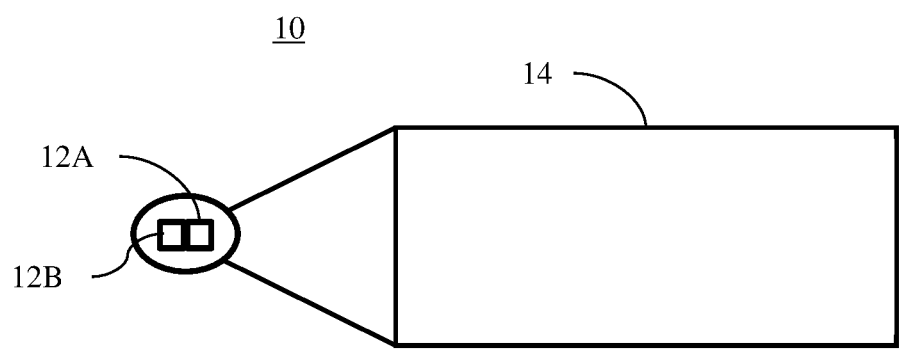
FIG. 2 is a cross-section view of another embodiment of a multispectral calibration source for medical emission tomography imaging.

FIG. 2 shows another embodiment of the calibration source 10. Two pellets 12A, 12B are in the housing 14. FIG. 2 shows two pellets 12A, 12B, but three or more pellets may be used. Each pellet 12A, 12B forms a different active element of the calibration source 10 by including a different or different combination of radioisotopes. At least one or all radioisotopes of one pellet 12A is different than all of the radioisotopes of the other pellet 12B. In one embodiment, each pellet 12A, 12B includes a single radioisotope, which radioisotopes are different from each other.

As shown in FIG. 2, the pellets 12A, 12B are stacked directly adjacent to each other. There is no intervening housing or framework between the pellets 12A, 12B. Epoxy, sealant, or glue may be between the pellets 12A, 12B while being directly adjacent. In other embodiments, the pellets 12A, 12B are separated from each other in the housing 14, such as being separated by a support or frame. In one example, the pellets 12A, 12B are in opposite ends of the housing 14.

The pellets 12A, 12B are stacked along a center line of the longest dimension of the housing 14. Other orientations and/or positioning within the housing may be used.

In the example of FIG. 2, the pellets 12A, 12B have the same size and shape as each other. In other embodiments, the different pellets 12A, 12B have different sizes and/or shapes.

The housing 14 is steel or other metal but may be other material such as glass or ceramic. The housing 14 is of any thickness and form factor. Threading, sealant, and/or other materials or objects may be formed as part of the housing 14. For example, one end of the housing 14 is a threaded end cap that threads onto or into the rest of the housing 14.

In the examples of FIGS. 1 and 2, the housing 14 is formed from a cylinder with a conical end capped by a spherical portion. The angle of the conical end is set to allow for use of the calibration source 10 with a physically collimated detector. The angle limits the scattering or interference of the housing 14 with emissions from the pellet 12, providing a desired field of view for the calibration source 10.

The spherical portion is at one end of the housing 14, providing a visual indication of the location of the pellet 12 and/or source of emissions. In other embodiments, the pellet 12 is positioned on or in the housing 14 at a location other than the end.

The cylindrical portion may be cuboid, polyhedron, or another shape. Other shapes may be used for any part of the calibration source 10.

In one embodiment, the spherical portion of the housing 14 around the pellet 12 has an outer diameter less than 0.25 inches. Larger outer diameters may be used for the sphere or other shape covering the pellet 12. The cylindrical portion of the housing (e.g., end opposite the sphere and/or pellet 12) has an outer diameter of 0.3 inches or larger. Any relative sizing may be provided.

The surface of the cylindrical portion and/or other parts of the housing 14 may be smooth or rough (e.g., ridged). Holes, indents, latches, knobs, and/or other structure may be included on the outer surface of the housing 14. In one embodiment, the housing 14 is shaped and sized for placement in a dosimeter, such as providing the dimensions and shape discussed above where the length and greatest diameter perpendicular to the length are sized to fit in a cylindrical interior chamber of a dosimeter.

The housing 14 encloses the pellet 12 or pellets 12A, 12B. The pellet 12 is entirely surrounded by the housing 14. For example, the partial sphere of the housing 14 surrounds most of the pellet 12. An epoxy support connects with another part of the pellet 12 where the housing 14 surrounds the epoxy support, entirely enclosing the pellet 12. In other embodiments, one or more parts of the pellet 12 are not enclosed, such a providing a window or hole through the housing 14 to the pellet 12.

The calibration sources 10 of FIGS. 1 and 2 include multiple radioisotopes. As a result, a fewer number of calibration sources 10 are likely to be needed at a clinical site. The one source 10 may be used for calibration and/or cross-calibration for multispectral imaging and/or where a detector is to be used at different times for imaging from different energies.

Figure 3:
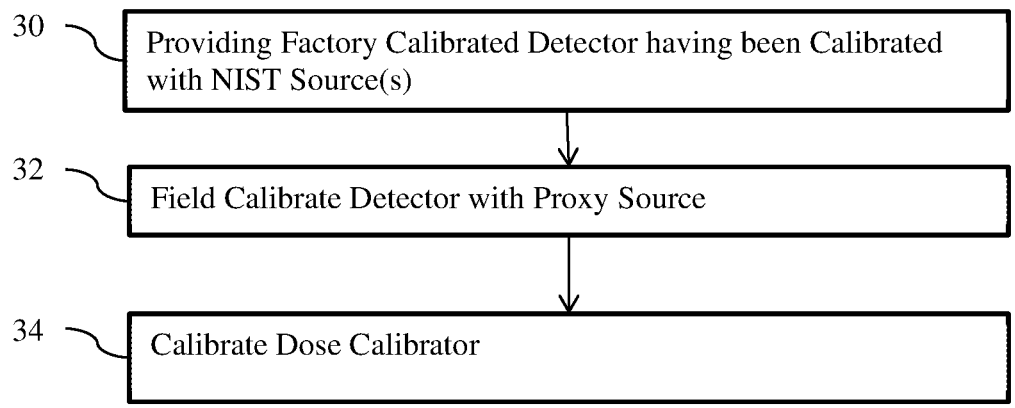
FIG. 3 is a flow chart diagram of one embodiment of a method for calibration of medical emission tomography using a proxy.
Figure 4:
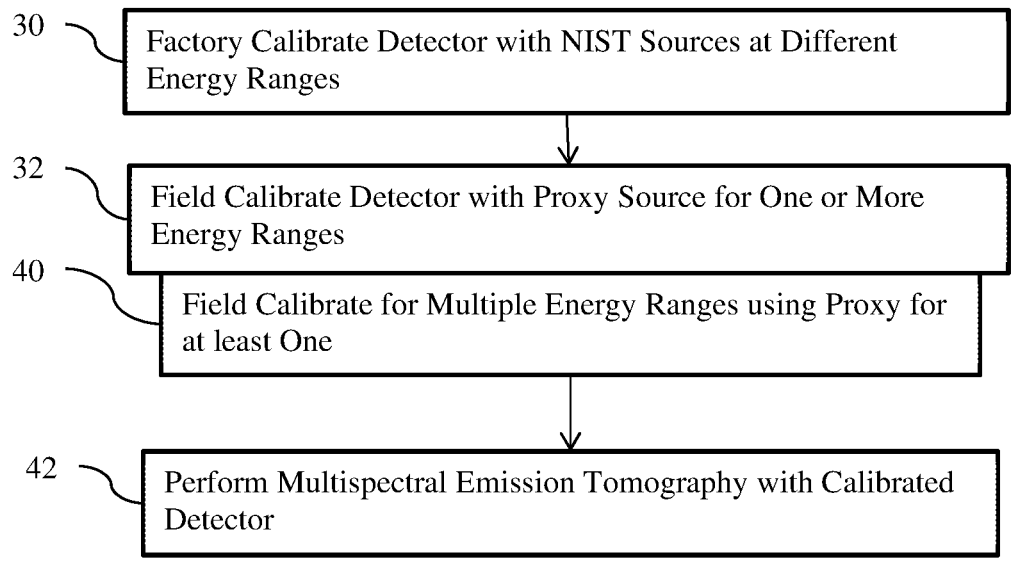
FIG. 4 is a flow chart diagram of an embodiment of a method for multispectral calibration of medical emission tomography using a proxy.

FIGS. 3 and 4 are flow charts for two embodiments of methods for calibration for medical emission tomography. Both embodiments are directed to use of a calibrated source as a proxy source. The proxy source may be a multispectral calibrated source 10 or another calibrated source with only one included radioisotope. The proxy source includes one or more isotopes that are different than used for factory calibration. A different peak energy or different peak energies are used to calibrate with the proxy. In other embodiments, the same isotope is used for both factory and field calibration (i.e., no proxy).

The calibration may be for multispectral tomography as shown in FIG. 4. The detector is calibrated at two or more different energies or energy ranges. The multispectral calibration source provides emissions at two or more (e.g., all) of the energies or energy ranges of interest, resulting in fewer calibration sources being needed for calibration for multispectral tomography. Where the emission tomography is not multispectral (e.g., the detector is going to be used for a single isotope, peak energy, and/or energy range), the multispectral source 10 may allow for calibration at different energies and/or energy ranges for use with different isotopes for different patients or for different times, resulting in having to stock fewer calibration sources in the field.

The calibration source is used for any calibration process. For example, the cross-calibration described in US published application 2015/0196268 is performed. As another example, the calibration described in US published application 2014/0371580 is performed. The calibration source is used to field calibrate the emission tomography detector and/or used for calibrating the dosimeter or other dose calibrator. For example, the calibration source is used with the dose calibrator of PCT/US2020/070520. In other embodiments, correlation and cross correlation (i.e., linearization and ratio) are used to calibrate over energy ranges based, at least in part, on the calibration source. A non-linear fitting to extrapolate (i.e., minimize objective function) the calibration across multiple energy ranges may be used.

Additional, different, or fewer acts than shown in FIGS. 3 and 4 may be provided. For example, acts 34, 40, and/or 42 are not performed. As another example, acts for performing emission tomography are provided.

In act 30, an emission tomography system is provided, such as a SPECT or PET imager. The emission tomography system includes a detector, such as one or more planar gamma cameras, a ring of PET detectors, or a dual layer Compton detector. The detector was factory calibrated. One or more factory calibration sources, such as NIST traceable calibration sources of Co57, Sn157, and/or Tn113, were used to calibrate the detector. The factory calibration may be by class of detectors or for the specific detector. The factory calibration provides identification of specific energy bins of the detector with one or more specific energies. Using correlation, extrapolation, and/or other modeling, the detector may be calibrated over one or more ranges of energy.

In one embodiment, the detector was calibrated with multiple radioisotopes. The calibration is for multiple energies and/or energy ranges. Where one or more proxy sources are to be used in the field, the calibration at the factory does not use one or more of the isotopes to be used in field calibration.

In act 32, a technician field calibrates the emission tomography detector. The calibration uses a calibrated source of a radioisotope. Where a proxy source is used, the radioisotope is different than the radioisotope(s) used for the factory calibration. The calibration source is a proxy source. The emission tomography detector is field calibrated with a calibrated source for a radioisotope or radioisotopes. One or more radioisotopes of the calibrated source used to measure detector sensitivity at the clinical site is different than any of the radioisotopes used for factory calibration (e.g., used for class standard). The calibration source provides a proxy for the radioisotope used for factory calibration.

In one embodiment, the calibration is for multiple energy ranges in act 40. For each energy range (e.g., low, mid, and high), a different radioisotope is used for the factory determined sensitivity or calibration. For example, Co57, Sn157, and Tn113 are used to determine a class sensitivity at three energy ranges. At the clinical site, one or more of the energy ranges are calibrated using a proxy source with an isotope other than any of Co57, Sn157, and Tn113. Using the proxy may result in less accuracy and/or precision since the energy peaks for the factory and clinical site calibrations are not identical, but costs and burdens in stocking calibration sources at the clinical site are reduced.

A proxy source may be used for one or more of multiple energy ranges. For example, three energy ranges are calibrated (i.e., identifying the line or curve of detector sensitivity over energy for each of three ranges). At the clinical site, one, two, or all three energy ranges are calibrated with proxy source(s) that include different isotopes than used for the class sensitivity of the factory calibration. In one embodiment, one or more of the energy ranges uses a calibrated source with the same isotope used in the factory calibration.

In one embodiment, a multispectral calibrated source is used in the field calibration. One, more, or all of the isotopes of the multispectral calibrated source are proxies. For example, the calibrated source at the clinical site includes a plurality of radioisotopes: including a proxy isotope (not including at least one radioisotope used for factory calibration) and including one of the multiple radioisotopes used in the factory calibrating as an anchor. The multispectral source includes both a same isotope and a proxy isotope. In other embodiments, the multispectral source includes only proxy isotopes or only the same isotopes (i.e., anchor isotopes) as used for factory calibration. The multispectral source may be one of the calibrated sources of FIG. 1 or 2 or a different calibrated sources including multiple isotopes.

The calibration models or fits to determine the energy bins or detected energy from the emission tomography detector to specific energies. The calibration is for a specific energy or energy range. The calibration may be multispectral, providing calibration for energies or energy ranges.

In act 34, the technician calibrates a dose calibrator. For example, a calibration source that is a proxy source is placed in a gas chamber dosimeter. As another example, a multispectral source with or without proxy is input in the dosimeter. The measurements from the source are compared to the expected or known energy emissions, and the dose calibrator readings are adjusted to account for the difference. This adjustment may be modeled over an energy range or ranges or may be determined for a specific energy or energies.

In one embodiment, the calibration is a multispectral calibration over three or more energy ranges using the approach in US Published Application No. 2015/0196268. The calibration is for emission tomography, such as SPECT. Raw PRE reconstruction data within an energy window, at a subtended angle, and theoretical sensitivity is used to determine the sensitivity, such as a planar sensitivity of a gamma camera. For factory calibration, the emission tomography design specifications, such as for the gamma camera class, are used to determine class standard sensitivity (i.e., factory calibration by simulation). Source and system simulation may be used to establish the class standard as an alternative to measurements from calibrated sources. Cross-calibration of an actual calibrated source or sources to design may be used in the factory calibration to remove a need for a class standard. Actual measurements by one or more detectors of the class may be used. Multiple stages of cross-correlation beyond one or two long lived radioisotopes may be used to calibrate across more than two energy ranges. A ratio may be used in calibration, such as calibration for specific energies. In other embodiments, a fit of a data model to data with minimization of an objective function is used to calibrate across an energy range. By using a reference isotope in field calibration, such as a multispectral and/or proxy source, the cross-calibration may be computed without modeling the reference source. The result is fewer sources having to be maintained at the clinical site.

In act 42, the activity concentration is estimated. The calibrated or cross-calibrated emission tomography detector and/or dosimeter measured dose is used to estimate activity concentration for a patient. The activity concentration in a patient having received a liquid radiotracer is determined as part of reconstruction by the emission tomography system. After ingesting or injecting the radiotracer into the patient, the patient is positioned relative to the detector and/or the detector is positioned relative to the patient. Emissions from the radiotracer within the patient are detected over time. To determine the locations within the patient at which the emissions occurred, the detected emissions are reconstructed into an object space.

For reconstruction, the activity concentration (e.g., quantitative SPECT) is reconstructed using a system matrix. Distribution of emissions in a volume or image data is reconstructed from the detected emissions. The quantity or amount of uptake for each location (e.g., voxel) is estimated as part of the reconstruction in computed tomography. The SPECT imaging system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., counts), the system matrix, isotope properties (e.g., calibration-based corrected dose value from the dosimeter), and biology. The system matrix represents mechanical properties of system, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The reconstruction uses the system model representing various aspects of the detection of the emissions, including modeling the imaging physics. The imaging physics includes aspects of the SPECT system, such as calibration of the SPECT system. The system model includes the detector sensitivity, such as the system specific sensitivity to the liquid radiotracer(s) used in the patient. The system specific sensitivity (e.g., gamma camera planar sensitivity in SPECT) is used in the estimation of the activity concentration. The system specific sensitivity to the liquid radiotracer calculated in cross-calibration is used. For example, the estimation is a function of class standard sensitivities of factory calibration and the measured system specific sensitivity to the calibrated or long-lived source. The corrected dose is included as part of the system matrix or as a separate isotope data used in reconstruction. Similarly, calibration at different energies and/or energy ranges is used in multispectral tomography, such as multiplexed collimation or Compton.

Specific uptake values (SUVs) may be calculated by the processor of the emission tomography system. The activity concentration represents the amount of uptake at each location. This amount of uptake is a measure of emitted radiation, so is not normalized for the radiation dose provided to the patient. As a result, comparing uptake from different times may not be useful unless the same doses are provided. By calculating the SUV, uptake normalized for dose is provided, allowing comparison of different measures. The SUV for each location or for some of the locations is calculated. The SUV is a function of the activity concentration for that location and the corrected dose value.

Figure 5:
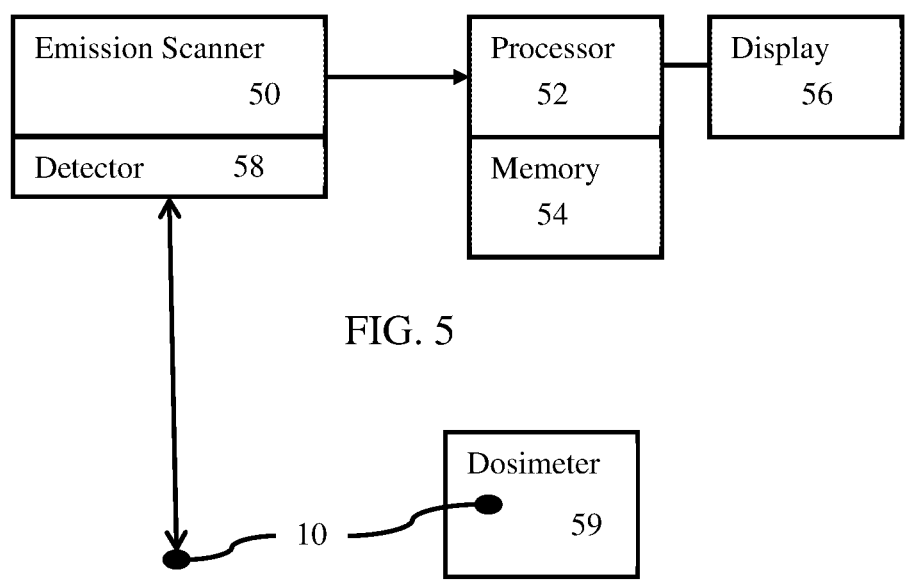
FIG. 5 is a block diagram of one embodiment of an emission tomography system for calibration.

FIG. 5 shows an emission tomography system for calibration and imaging. The system includes an emission scanner 50, a processor 52, a memory 54, and a display 56. The processor 52, memory 54, and/or display 56 are part of the emission scanner 50 or are separate (e.g., a computer or workstation). A dosimeter 59 is provided for correcting dose injected into the patient. Additional, different, or fewer components may be provided.

The emission scanner 50 is a SPECT, PET, or Compton system. The emission scanner 50 includes a detector 58. The detector 58 of FIG. 5 is shown as a planar gamma camera of a SPECT system but may be a ring detector of a PET or dual-layer detector of a Compton system. Other components may be provided, such as collimator.

The emission scanner 50, using the detector 58, detects emissions. For calibration, the detector 58 detects emissions from a proxy source and/or from a multispectral calibrated source 10. The calibration source 10 is used as a point source, which may be at any position in the 2D transverse direction relative to the detector 58 but is preferably centered. The emissions are measured with the point source at any distance from the detector 58 for calibration.

The calibrated source 10 is a long-lived, factory calibrated point source. Any size point source may be used, such as a 1 mm$^3$ vessel, with the long-lived radioisotope. The dose of the source 10 is known with any degree of accuracy. The dose is measured at a factory with equipment having greater accuracy than used in labs providing liquid radiotracers. The source 10 is positioned relative to the detector 58 for measuring detector or system specific sensitivity to the point source.

The emission scanner 50 may include a timer. The timer measures a period from activation of detection through to reaching a number of counts. The emission events detected by the detector 58 are counted over time to calculate the sensitivity. The emission scanner 50, using the processor 52 or another processor, is configured to measure the system specific sensitivity of the detector 58 to the long-lived calibrated source 10 and apply the resulting calibration in imaging a patient.

The emission scanner 50, using the processor 52 or another processor, is configured to reconstruct the imaged volume by applying a system model to the detected data. The emission scanner 50 accesses the detected emission events from the memory 54 or buffers to reconstruct. The system model includes a system specific sensitivity for the liquid radiotracer provided to the patient. This sensitivity is based on the calibration and is used for the reconstruction. The reconstruction also uses a dose value for the radiotracer applied to the patient. The calibration source 10 is used to calibrate the dosimeter in order to correct the dose (calibrate the dosimeter) measured by the dosimeter 59.

The processor 52 operates pursuant to stored instructions to perform various acts described herein, such as calculations or settings for or based on the calibration. The processor 52 is configured by software, firmware, and/or hardware to perform, control performance, and/or receive data resulting from any or all of the acts of FIG. 3 or 4.

In one embodiment, the processor 52 is configured to reduce variability due to dose and detector sensitivity of uptake values and activity concentration output by the emission tomography imaging system 50 (e.g., a SPECT scanner) for a patient. The processor 52 is configured to reduce variability as a function of a class standard sensitivity to a liquid radiotracer source and a system specific sensitivity to the calibration radiotracer source 10. The class standard sensitivities to a liquid radiotracer and to a long-lived point source are loaded from memory 54 or received by transfer. These sensitivities provide a ratio that may be used with the measured system specific sensitivity to a same or different source 10 for calculating, by the processor 52, the system specific sensitivity to the liquid radiotracer. Using dose calibrator liquid radiotracer sensitivity, the processor 52 is configured to calculate a cross-calibration or dose correction factor. The sensitivity is input to the processor 52 with user interface, loaded from memory 54, or transferred over a network. The correction factor and calculated system specific sensitivity may reduce variability in reconstruction and/or calculation of specific uptake values.

The processor 52 is configured to correct the input dose of the liquid radiotracer provided to the patient. The correction factor from calibration of the dosimeter is multiplied with the measured dose of the liquid radiotracer injected into the patient. Based on this corrected dose, the processor 52 is configured to calculate SUVs. The SUV at one or more locations are calculated by normalizing the activity concentration with the corrected dose. The resulting SUVs have less variability due to the system and/or dose, so more likely represent changes in metabolic function of the patient.

The detected emission events, calibration information, or other scan data is stored in the memory 54. The data is stored in any format. The memory 54 is a buffer, cache, RAM, removable media, hard drive, magnetic, optical, database, or other now known or later developed memory. The memory 54 may store data at different stages of processing, such as counts, time to reach a count, raw data representing detected events without further processing, filtered or thresholded data prior to reconstruction, reconstructed data, filtered reconstruction data, system model, projection data, thresholds, an image to be displayed, an already displayed image, or other data. The memory 54 or a different memory stores class standard sensitivities loaded into or provided to the emission scanner 50. The memory 54 or a different memory stores the cross-calibration factor and/or any of the sensitivities. For processing, the data bypasses the memory 54, is temporarily stored in the memory 54, or is loaded from the memory 54.

The memory 54 is additionally or alternatively a non-transitory computer readable storage medium with processing instructions. The memory 54 stores data representing instructions executable by the programmed processor 52. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 56 is a CRT, LCD, plasma screen, projector, printer, or other output device for showing an image. The display 56 displays calibration information, such as fit energy models for the detector sensitivity and/or correction factors for the dosimeter.

The display 56 may display an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. Alternatively or additionally, any quantities derived by the processor 52 may be displayed, such as SUVs and/or change in SUV. Other quantities may be determined, such as average SUV or activity concentration for a region, maximum SUV, peak SUV in a predetermined unit volume, variance in activity concentration, or total SUV.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A calibration source for medical emission tomography, the calibration source comprising:
   an epoxy pellet comprising a mix of cured epoxy and an active element with at least two different radioisotopes, wherein at least one radioisotope of the at least two different radioisotopes is used for factory calibration and wherein at least one radioisotope of the at least two different radioisotopes is a proxy source that is not used for factory calibration; and
   a housing enclosing the epoxy pellet.

2. The calibration source of claim 1 wherein the active element comprises a multispectral source with at least one different energy peak for each of the at least two different radioisotopes.

3. The calibration source of claim 1 wherein the epoxy pellet is less than 0.15 inches in a longest dimension and the housing encloses the epoxy pellet, the epoxy pellet in a first end of the housing.

4. The calibration source of claim 3 wherein the first end of the housing forms a sphere around the epoxy pellet, an outer diameter of the sphere less than 0.25 inches, and wherein the housing has a second end opposite the first end, the second end forming a cylinder having an outer diameter greater than 0.3 inches.

5. The calibration source of claim 1 wherein the calibration source comprises a single photon emission computed tomography or positron emission tomography calibration source.

6. The calibration source of claim 1 wherein the housing is shaped and sized for placement in a dosimeter or a dose calibrator.

7. The calibration source of claim 1 wherein the at least two radioisotopes comprise a first radioisotope common to a factory calibration source and a second radioisotope, wherein the first radioisotope comprises Co57, Se75, Sn157, Cs137, or Tn113 and wherein the second radioisotope comprises Lu177, Rh186, St89, Sa153, Bi213, Pb212, Ga157, Bo10, Y90, P32, Ce131, Pa103, Ra223, Ac225, Th232, Po212, or I131.

8. A calibration source for medical emission tomography, the calibration source comprising:
   a first pellet comprising a mix of cured epoxy and a first active element of a first radioisotope, wherein the first radioisotope is an isotope used for factory calibration;
   a second pellet comprising a mix of cured epoxy and a second active element of a second radioisotope different than the first radioisotope, wherein the second radioisotope is a proxy source that is not used for factory calibration; and
   a housing enclosing the first and second pellets, wherein the first pellet is stacked directly adjacent the second pellet within the housing.

9. The calibration source of claim 8 wherein the first pellet has a same size and shape as the second pellet.

* * * * *